United States Patent
Wang et al.

(10) Patent No.: US 9,023,890 B2
(45) Date of Patent: *May 5, 2015

(54) NITRATE ESTERS AND THEIR USE FOR THE TREATMENT OF MUSCLE AND MUSCLE RELATED DISEASES

(75) Inventors: Guqi Wang, Charlotte, NC (US); Qi Long Lu, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 1101 days.

This patent is subject to a terminal disclaimer.

(21) Appl. No.: 12/629,230

(22) Filed: Dec. 2, 2009

(65) Prior Publication Data

US 2011/0130455 A1 Jun. 2, 2011

(51) Int. Cl.
| | |
|---|---|
| A61K 31/21 | (2006.01) |
| C07C 203/08 | (2006.01) |
| A61K 31/27 | (2006.01) |
| A61K 45/06 | (2006.01) |
| C07C 203/04 | (2006.01) |

(52) U.S. Cl.
CPC ............. *A61K 31/21* (2013.01); *A61K 31/27* (2013.01); *A61K 45/06* (2013.01); *C07C 203/04* (2013.01)

(58) Field of Classification Search
USPC .......................................... 514/509; 558/480
See application file for complete search history.

(56) References Cited

U.S. PATENT DOCUMENTS

| | | | |
|---|---|---|---|
| 3,251,739 A | 5/1966 | Petersen et al. | |
| 4,112,115 A * | 9/1978 | Coghlan ............... | 514/509 |
| 5,366,997 A | 11/1994 | Keefer et al. | |
| 5,455,279 A | 10/1995 | Lipton | |
| 5,693,676 A | 12/1997 | Gorfine | |
| 5,698,738 A | 12/1997 | Garfield et al. | |
| 5,958,427 A | 9/1999 | Salzman et al. | |
| 6,143,746 A | 11/2000 | Daugan et al. | |
| 6,310,052 B1 | 10/2001 | Thatcher et al. | |
| 6,365,579 B2 | 4/2002 | Thatcher et al. | |
| 6,436,996 B1 | 8/2002 | Vitek et al. | |
| 6,677,374 B2 | 1/2004 | Thatcher et al. | |
| 6,916,835 B2 | 7/2005 | Thatcher et al. | |
| 6,967,102 B1 | 11/2005 | Anderson | |

FOREIGN PATENT DOCUMENTS

| | | |
|---|---|---|
| EP | 1 676 570 A1 | 7/2006 |
| EP | 2329862 A1 | 6/2011 |
| JP | 58-000913 | 1/1983 |
| WO | WO 99/59575 | 11/1999 |
| WO | WO 00/76318 | 12/2000 |
| WO | WO 2006/130982 | 12/2006 |
| WO | WO 2007/088050 | 8/2007 |
| WO | WO 2007/088123 | 8/2007 |

OTHER PUBLICATIONS

The Free Dictionary.com, "Angina" (Retrieved on Jun. 17, 2012 from the Internet: <URL: http://medical-dictionary.thefreedictionary.com/angina).*
Valtonen (Curr Med Res Opin, vol. 3, No. 6, abstract; 1975).*
Database WPI; Week 198307; Thomson Scientific, London, GB; AN 1983-15774K; XP002627588; & JP 58 000913 A (Nitto Electric Ind Co); Jan. 6, 1983; Abstract.
Extended European Search Report for European Patent Application No. 10193482.6 dated Mar. 21, 2011; 10 pages.
Wang et al., "Development of a Nitric Oxide-Releasing Analog of the Muscle Relaxant Guaifenesin for Skeletal Muscle Satellite Cell Myogenesis," *Molecular Pharmaceutics*, Mar. 24, 2009.
Folland et al.; "The Influence of Nitric Oxide on in Vivo Human Skeletal Muscle Properties;" dated Jun. 1, 2000; Acta Physiologica Scandinavica, vol. 169, No. 2.
Ito Y et al.; "Supported Vasodilating Compsn. for Local Application—Comprising Sticky Material and Nitrite-type Vasodilator on Flexible Support;" dated Jan. 6, 1983; WPI/Thomson, vol. 1983, No. 7.
European Search Report for Application No. EP-12170542, dated Aug. 22, 2012.
Office Action for Chinese Application No. 201010625236.6 dated Jul. 27, 2012.
Office Action for European Application No. 10 193 482.6 dated Jan. 28, 2015.

* cited by examiner

*Primary Examiner* — Samantha Shterengarts
(74) *Attorney, Agent, or Firm* — Alston & Bird LLP

(57) ABSTRACT

Alkyl nitrate ester compounds are provided for the delivery of nitric oxide to targeted muscle tissues, and in particular, to normal and dystrophic muscles. In one aspect, nitrate ester compounds are provided having the following formula:

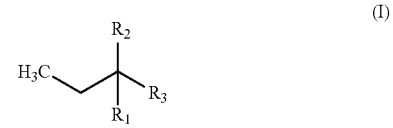

(I)

wherein,
$R_1$ is $ONO_2$, $CH_2ONO_2$, $C_nH_{2n+1}OH$, $C_nH_{2n+1}OH$, or $CH_2CH_2CH_3$, or H;
$R_2$ is $ONO_2$, $CH_2ONO_2$, $C_nH_{2n'+1}OH$, $C_nH_{2n'+1}OH$, $CH_2CH_2CH_3$ or H; and
$R_3$ is $ONO_2$, $CH_2ONO_2$, $C_{n''}H_{2n''+1}OH$, $C_{n''}H_{2n''+1}OH$, $CH_2CH_2CH_3$ or H;
wherein n is an integer from 0 to 9, n' is an integer from 0 to 9, and n" is an integer from 0 to 9, and n+n'+n"≤9, and wherein at least one of $R_1$, $R_2$, and $R_3$ is an ester nitrate selected from the group consisting of $ONO_2$, $CH_2ONO_2$, and combinations thereof.

8 Claims, 5 Drawing Sheets

NITRATE ESTERS AND THEIR USE FOR THE TREATMENT OF MUSCLE AND MUSCLE RELATED DISEASES

FIELD OF THE INVENTION

The present invention relates generally to the delivery of nitric oxide (NO) and muscle relaxant to muscle tissues, and in particular to the treatment of muscular disorders and the improvement of muscle functions.

BACKGROUND OF THE INVENTION

Muscular dystrophy refers to a group of genetic muscle diseases that causes weakening and wasting of the muscles. Generally, muscular dystrophies are characterized by progressive skeletal muscle weakness, defects in muscle proteins, and the death of muscle cells and tissue. The most common forms of muscular dystrophies include Duchenne, Becker, limb girdle, congenital, facioscapulohumeral, myotonic, oculopharyngeal, distal, and Emery-Dreifuss. Of these, Duchenne muscular dystrophy (DMD) is the most common form affecting 1 in every 3,500 live male births. Becker muscular dystrophy (BMD) is a milder form of the disease.

Deficiency of dystrophin in dystrophic muscles results in loss of a large transmembrane protein complex, named dystrophin sarcolemma integrity. The "dystrophin-glycoprotein complex" (DGC) helps anchor the structural skeleton within the muscle cells, through the outer membrane of each cell, to the tissue framework that surrounds each cell.

Many signaling molecules, such as neuronal nitric oxide synthase (nNOS), associate with DGC. Loss of DGC in dystrophic muscle contributes to DMD pathogenesis. NO is an important regulatory signal for a large number of physiological and pathophysiological processes in the body. NO is produced by nNOS in the muscle. Without dystrophin, the membrane associated nNOS is not properly anchored to the sarcolemma and is instead mislocalized to the cytoplasm. This mislocalization results in decreased nNOS and NO levels. The reduction of nNOS and NO may lead to impaired skeletal muscle contraction, vascular dilation, and muscle damage.

Muscle tissue in adult vertebrates regenerates from reserve cells or stem cells or inactive myoblasts called satellite cells. Satellite cells are distributed throughout muscle tissue in close juxtaposition to muscle fibers, and are mitotically quiescent in adult muscle when injury, disease or muscle growth is absent. Following muscle fiber injury or during the process of recovery from disease, satellite cells re-activate and re-enter the cell cycle. Once activated, the satellite cells proliferate and the daughter cells (progeny cells termed myoblasts) either 1) fuse with existing multinucleated muscle fibers to contribute new nuclei that support muscle growth or regeneration, or 2) fuse with one another to form a new length of multinucleated muscle fiber called a myotube. Satellite cells of normal skeletal muscle provide a constant and renewable source of myogenic precursor cells which allows for skeletal muscle repair and regeneration throughout mammalian life.

NO mediates activation of satellite cells to enter the cell cycle. Such cycling provides new precursor cells for the skeletal muscle growth and muscle repair following injury or disease. Reduced NO production impairs muscle regeneration in normal muscle and exacerbates muscular dystrophy. Accordingly, developing a system to deliver NO to skeletal muscle and thereby manipulate the regulation of satellite cell activation has the potential to promote normal function in injured muscle tissue and possibly be used to treat neuromuscular disease.

BRIEF SUMMARY OF THE INVENTION

The present invention is directed to a composition and associated method for the treatment of muscles and muscle related disorders and diseases. In particular, the present invention provides a class of nitrate ester compounds that can be used to deliver nitric oxide (NO) to targeted muscle tissue. Compounds and compositions in accordance with the present invention have been shown to increase myogenesis in adult muscle tissue as well as decrease creating kinase. As a result, compounds and compositions in accordance with the present invention can be used to treat injured and diseased muscle tissue. Additionally, compositions and compounds in accordance with the present invention have been shown to improve exercise performance and delay dystrophophic/atrophic pathogenesis in dystrophic muscle.

In addition to delivering nitric oxide to the targeted muscles, the inventive nitrate esters also have muscle relaxant and/or sedative properties. Muscle relaxation is beneficial for muscle regeneration and repair. Muscle relaxation is beneficial for muscle regeneration and repair. Muscle relaxants are believed to work through the nervous system by decreasing nerve impulses from the brain and spinal cord that lead to tensing or tightening of muscle fibers. Although, muscle relaxants do not heal muscle injuries, they reduce discomfort, and may add benefit to recovery. For example, in muscular dystrophy, the muscle fibers are especially susceptible to contraction induced muscle damage. Slightly impairing the contraction machinery by relaxants or sedatives may suppress muscle degeneration and injury.

In one embodiment, the present invention is directed to nitrate esters having the following formula:

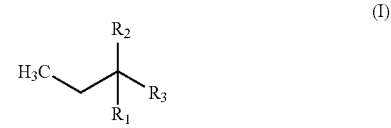

wherein, $R_1$ is $ONO_2$, $CH_2ONO_2$, $C_nH_{2n+1}OH$, $C_nH_{2n+1}OH$, or $CH_2CH_2CH_3$, or H;

$R_2$ is $ONO_2$, $CH_2ONO_2$, $C_nH_{2n'+1}OH$, $C_nH_{2n'+1}OH$, $CH_2CH_2CH_3$ or H; and $R_3$ is $ONO_2$, $CH_2ONO_2$, $C_{n''}H_{2n''+1}OH$, $C_{n''}H_{2n''+1}OH$, $C_{n''}H_{2n''+1}OH$, $CH_2CH_2CH_3$ or H;

wherein n is an integer from 0 to 9, n' is an integer from 0 to 9, and n" is an integer from 0 to 9, and n+n'+n"≤9, and wherein at least one of $R_1$, $R_2$, and $R_3$ is an ester nitrate selected from the group consisting of $ONO_2$, $CH_2ONO_2$, and combinations thereof.

In a preferred embodiment, the present invention is directed to the treatment of muscles and muscle related diseases comprising the step of administering a therapeutically effective amount of a composition or compound having the following formula:

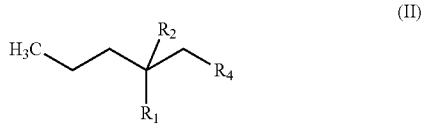

(II)

$R_2$ is $CH_2ONO_2$ or H;
$R_1$ is $CH_2CH_2CH_3$; and
$R_4$ is $ONO_2$.

Embodiments of the present invention also provide a pharmaceutical composition comprising the compound or salt, and a pharmaceutically acceptable carrier. The pharmaceutical composition may be used for promoting formation of muscle tissue or promoting repair of damaged muscle tissue in normal (i.e., non-dystrophic) muscle or for regulating satellite cell proliferation in dystrophic muscle. In one particular embodiment, compounds and compositions in accordance with the present invention may be used for treating muscular dystrophy, promoting muscle growth, and improving muscle functions.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
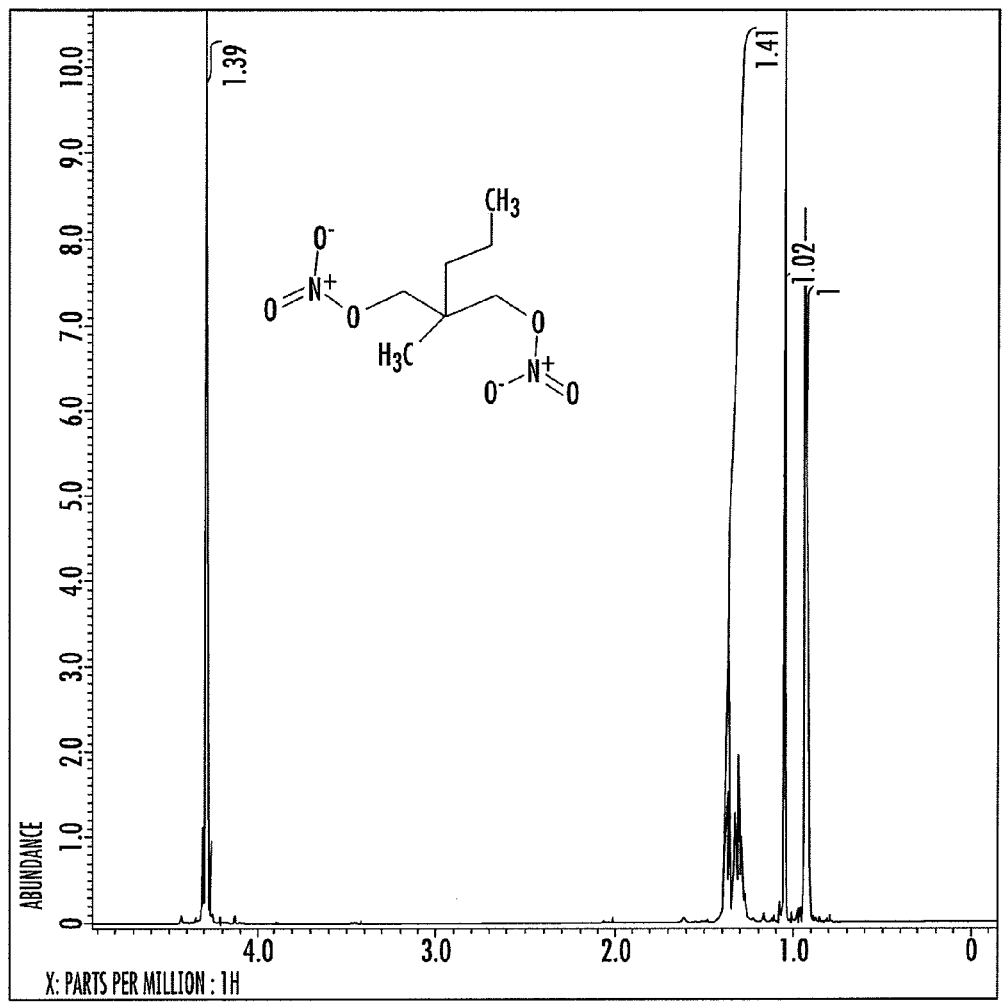
FIG. 1 is an NMR spectra of 2-methyl-2-[(nitrooxy)methyl]pentyl nitrate.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention is directed to compounds and compositions for the treatment of muscular tissue, improvement of muscle performance, and in particular muscular related diseases. In particular, the present invention is directed to the treatment of muscular diseases in which muscle regeneration is frustrated or interfered. For example, the present invention can be used to treat muscle diseases associated with genetic mutations of pathways involving genes for muscle regulatory proteins, such as MyoD, myf5, myogenin, pax7, follistan, and the like. More particularly, compounds and compositions in accordance with the present invention can be used in the treatment of regenerating damaged muscle tissue in normal muscle, such as following an injury, traumatic or therapeutic loss of muscle. Additionally, the compounds and compositions in accordance with the present invention can be used to treat dystrophic muscles, conditions relating to atrophy or wasting of the muscle. In a further aspect of the present invention, compounds and compositions in accordance with the present invention can be used to improve exercise performance and endurance, conditions relating to sports, military and ageing uses. The compounds and compositions in accordance with the present invention can also be used to in cosmetic products to reduce and prevent form of ageing lines (frown or worry lines), folds and wrinkle.

Compounds and compositions in accordance with the present invention are directed to a class of nitrate esters analogs that are capable of releasing nitric oxide (NO) to muscles. In one embodiment, the present invention is directed to the use of compound (I) below for the treatment of muscles and muscle related diseases.

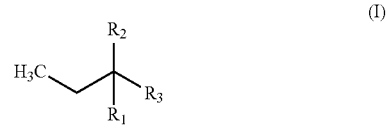

(I)

wherein,
$R_1$ is $ONO_2$, $CH_2ONO_2$, $C_nH_{2n+1}OH$, $C_nH_{2n+1}OH$, or $CH_2CH_2CH_3$, or H;
$R_2$ is $ONO_2$, $CH_2ONO_2$, $C_nH_{2n'+1}OH$, $C_nH_{2n'+1}OH$, $CH_2CH_2CH_3$ or H; and
$R_3$ is $ONO_2$, $CH_2ONO_2$, $C_{n''}H_{2n''+1}OH$, $C_{n''}H_{2n''+1}OH$, $CH_2CH_2CH_3$ or H;
wherein n is an integer from 0 to 9, n' is an integer from 0 to 9, and n" is an integer from 0 to 9, and n+n'+n"≤9, and wherein at least one of $R_1$, $R_2$, and $R_3$ is an ester nitrate selected from the group consisting of $ONO_2$, $CH_2ONO_2$, and combinations thereof.

In a preferred embodiment, the present invention is directed to compound (II) below and use thereof in the treatment of muscles and muscle related diseases.

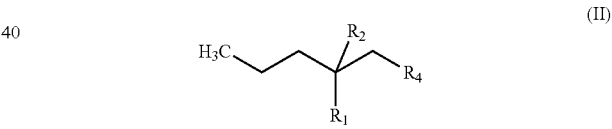

(II)

wherein
$R_2$ is $CH_2ONO_2$ or H;
$R_1$ is $CH_2CH_2CH_3$; and
$R_4$ is $ONO_2$.

The compounds and compositions of the present invention may be provided to muscle cells by any suitable means, including direct administration (e.g., in vitro by addition to culture medium, or in animals in vivo locally by injection or topical administration at a treatment site) or systemically (e.g., parenterally or orally). In one embodiment, the compounds and compositions comprise part of a physiologically acceptable solution so that in addition to delivery of the desired agent to the target cells, the solution does not otherwise adversely affect the electrolyte and/or volume and/or metabolism of the cells or tissue or subject.

The pharmaceutical compositions and compounds as utilized in this invention can be administered by intranasal, oral, inhalational, enteral, topical, intrauterine, vaginal, sublingual, rectal, intramuscular, intrapleural, intraventricular, intraperitoneal, ophthalmic, intravenous, or subcutaneous means.

If desired, a given compound or composition may be adapted to different situations by association with a suitable molecule. For example, NO donors may be made more soluble or dispersible in physiological solutions than the corresponding original form The compositions containing the compound of the present invention may be supplied in liquid or solid form. Compositions in accordance with the present invention may further include solvents, diluents, excipients, preservatives, emulsifiers, compounds for adjusting odor, taste, pH or the like.

The formulations can be administered with or without additional carrier or diluent by the oral, systemic injections, percutaneous, transmucosal, or other typical route. Pharmaceutical formulations in accordance with the present invention may be administered orally in caplet, tablet, particle, granule, or powder forms. The present invention provides a method of treating and/or ameliorating the effects muscle injury and/or muscle related diseases by administering a therapeutically effective amount and/or a prophylactic amount of the aforementioned nitrate esters or a pharmaceutically acceptable salt thereof, to a sufferer in need thereof. According to the present invention, a "therapeutically effective amount" of a compound, combination or pharmaceutical composition of the invention is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect. Typical dosage amounts may range from about 0.1 to 1,000 mg/kg body weight, and in particular from about 1 to 100 mg/kg body weight. In one embodiment, the dosage amount is from about 20 to 50 mg/kg body weight.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment, dosage forms (compositions) of the inventive composition may contain about 0.1 microgram to 1,000 micrograms of active ingredient per unit, and in particular, from about 2 to 80 micrograms of active ingredient per unit.

For intravenous delivery, a unit dose of the nitrate ester formulation will generally contain from 0.2 to 200 micrograms per kg body weight and preferably will contain from 1 to 100 micrograms, in particular 10, 15, 20, 30, 40, 50, 60, 70, or 80 micrograms per kg body weight (µg/kg body weight). The composition may be administered once or more times a day, or one or more times a week, for example 2, 3 or 4 times daily, or 2, 3 or 4 times weekly, and the total daily dose for a 70 kg adult will normally be in the range 1.0 to 10 micrograms. Preferred intravenous dosage ranges from 10 ng to 200 µg, preferably 2 to 200 µg, more preferably 10 to 100 µg of metal per kg of body weight. Alternatively the unit dose may contain from 2 to 20 micrograms of metal-thiol and be administered in multiples, if desired, to give the preceding daily dose. In these pharmaceutical compositions, the active ingredient will ordinarily be present in an amount of about 0.5-95% by weight based on the total weight of the composition.

For use in the treatment of targeted muscle injuries or muscle related disorders, by way of general guidance, a daily oral dosage of the active ingredient (i.e., nitrate ester analog) can generally range from about 0.02 to 2 mg/kg of body weight. In a preferred embodiment, the nitrate ester active agent of the invention can be administered at dosages of 0.2 to 40 mg of the nitrate ester per kg of body weight when administered orally. It should be recognized that the dosage can be raised or lowered based on individual patient response. It will be appreciated that the actual amounts of active compounds used will vary according to the specific compound being utilized, the particular compositions formulated, the mode of application, and the particular site of administration.

For oral administration when the composition is in the form of a tablet or capsule, the active ingredient can be combined with an oral, non-toxic, pharmaceutically acceptable, inert carrier, including but not limited to, lactose, starch, sucrose, glucose, methyl cellulose, magnesium stearate, dicalcium phosphate, calcium sulfate, mannitol, sorbitol and the like. Additionally, when desired or necessary, suitable binders, lubricants, disintegrating agents, and coloring agents can also be incorporated into the mixture. Suitable binders may include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms may include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In some embodiments, the nitrate ester formulations of the present invention may also be coupled with soluble polymers as targetable drug carriers. Such polymers can include, for example, polyvinylpyrrolidone, pyran copolymer, polyhydroxypropylmethacrylamide-phenol, polyhydroxyethylaspartamidephenol, or polyethyleneoxide-polylysine substituted with palmitoyl residues. In one embodiment, nitrate ester formulations in accordance with the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The compositions described herein may be administered as part of a sustained-release formulation (i.e., a formulation such as a capsule or resin or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are biocompatible, and may also be biodegradable; preferably the formulation provides a relatively constant level of modulating agent release. The amount of modulating agent contained within a sustained-release formulation depends upon the site of implantation, the rate and expected duration of release and the nature of the condition to be treated or prevented.

It is noted that humans are generally treated longer than mice or other experimental animals exemplified herein. Accordingly, the length of the treatment generally may be proportional to the length or intensity or prior duration of the disease or pathophysiological process, and may further depend on the animal species, drug effectiveness and degree of effect required or recommended. The doses may be single doses or multiple doses over a period of one to several days or longer.

In one embodiment, the pharmaceutical compositions and compounds of the present invention are administered topically, especially when the target of treatment includes areas or organs readily accessible by topical application, including diseases of the eye, the skin, or the lower intestinal tract. Topical application may also be readily used to administer the combinations, compounds and compositions of the invention to tissue below the skin, such as muscle. Suitable topical formulations may be prepared for each of these areas or organs.

Topical application for the lower intestinal tract may be effected in a rectal suppository formulation or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

Formulations suitable for topical administration to the eye also include eye drops wherein the active ingredients were dissolved or suspended in a suitable carrier, especially an aqueous solvent for the active ingredients. The active ingredients were preferably present in such formulations in a concentration of 0.5 to 20%, advantageously 0.5 to 10% and particularly about 1.5% w/w.

One can use topical administration to deliver a compound of the invention by percutaneous passage of the drug into the systemic circulation of the patient. The skin sites include anatomic regions for transdermally administering the drug, such as the forearm, abdomen, chest, back, buttock, thigh and retroauricular area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin, or the formulation is applied directly on the skin in a prescribed amount and schedule.

Formulations suitable for topical administration include liquid or semi-liquid preparations suitable for penetration through the skin (e.g., liniments, lotions, ointments, creams, gels or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but not more than 5% w/w, or from 0.1% to 1% of the formulation.

When formulated in an ointment, the active ingredients may be employed with either paraffinic or a water-miscible ointment base. Alternatively, the active ingredients may be formulated in a cream with an emulsified cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include methocarbamol, longer-chain alcohols, dimethylsulfoxide and related analogs.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating.

Transdermal administration may be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, flavouring agents, colouring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, flavoring agents, coloring agents, and the like.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween™ 60, Span™ 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents, as well as anti-fungal agents. Perfumes or volatile agents that confer an odour on the composition while, by evaporating, they 'set' or dry a topical formulation/application, may also be included.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora Transmucosal drug dosage forms (e.g., tablet, suppository, ointment, pessary, membrane, and powder) are typically held in contact with the mucosal membrane and disintegrate and/or dissolve rapidly to allow immediate systemic absorption.

The compound can also be used in combination with a muscle relaxant. Examples of muscle relaxants that may be used in the present invention include phenylglyceryl ether and its derivatives, including methocarbamol, Guaifenesin (glyceryl guaiacolate), chlorphenesin, chlorphenesin carbamate, chlorzoxazone, carisoprodol, mephenesin, meprobamate, dantrolene, and 3-phenoxy-1,2-propanediol. Additionally, pharmaceutically acceptable salts of known muscle relaxants may also be used in the compositions, methods and uses of the present invention.

In addition, the nitrate esters of the present invention may also be used in combination with glucocorticoids in the treatment of muscular dystrophic patients by supplementing NO to ameliorate glucocorticoids induced satellite cell inactivation. Glucocorticoids therapy greatly reduces tissue inflammation and suppressed cytotoxic cells. However, glucocorticoids suppress endogenous NO production, which induces skeletal muscle atrophy, increases proteolysis, and impairs muscle recovery from injury. A therapy including the inventive nitrate esters may be an effective strategy for treatment of muscular atrophy and augment the therapeutic benefits of glucocorticoid treatment of DMD.

The invention may also be used for improving vascular function, and blood circulation in muscle to enhance muscle resistance to fatigue.

The invention may be used as part of rehabilitation procedures by stimulating muscle formation and/or growth, and thereby increasing muscle function after muscle disuse or wasting, e.g. after bedrest or confinement, stroke or coma-induced incapacitation, and inathletic activity.

The invention may be used as part of pre- or post-surgical procedures, or wound/burn recovery to promote or allow optimal or efficient repair of muscle damage by muscle regeneration rather than formation of scar tissue and fibrosis.

EXAMPLES

Figure 2:
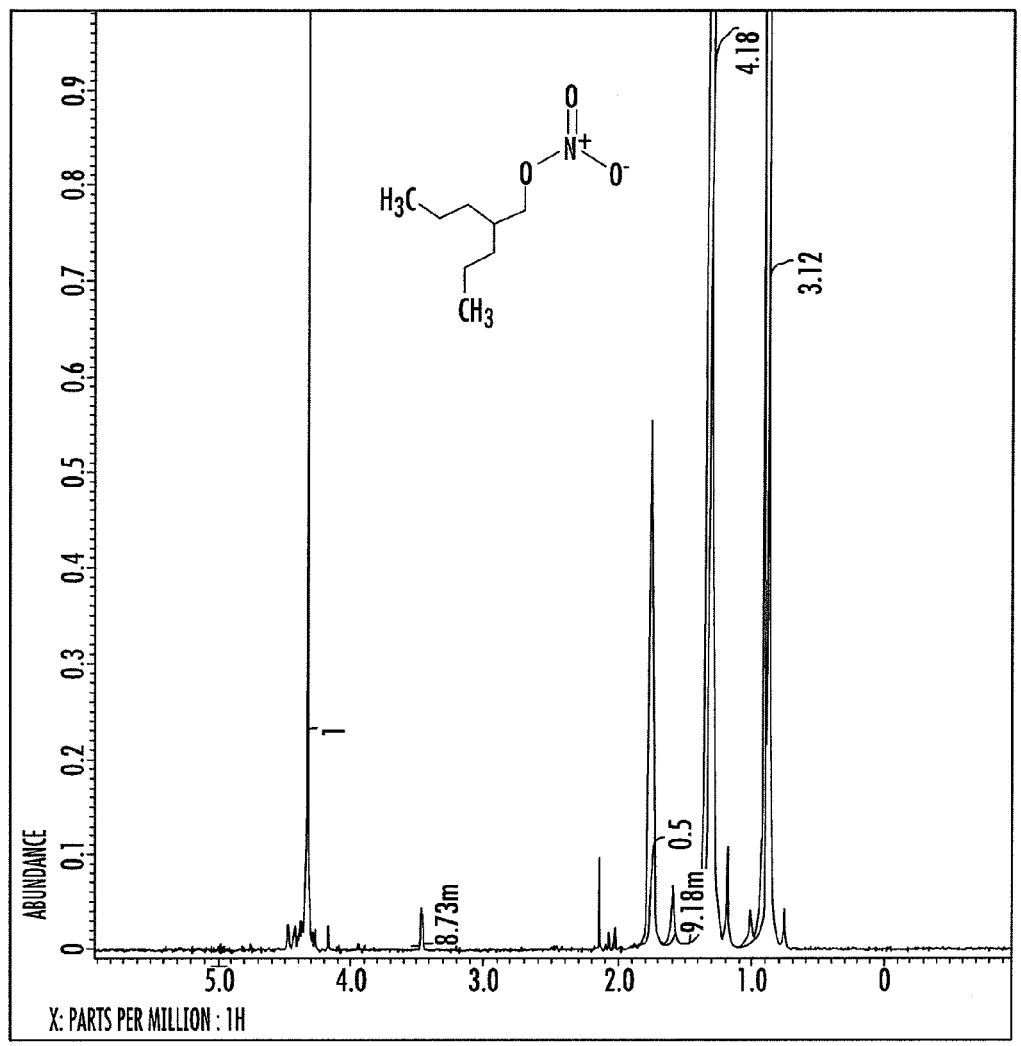
FIG. 2 is an NMR spectra of 2-propylpentyl nitrate.

Synthesis of 2-methyl-2-[(nitrooxy)methyl]pentyl nitrate and 2-propylpentyl nitrate The following provides a synthesis for 2-methyl-2-[(nitrooxy)methyl]pentyl nitrate. 22 mmole of concentrated nitric acid dropwise into 10 mL of acetic anhydride under stirring and cooling in an ice bath. Following the addition of the nitric acid, 20 mmole of an alkyl alcohol was added in small amounts to the solution with cooling at 15° C. and allowed to react at room temperature for an hour. The reaction mixture was poured into 100 mL of ice cold water. The product was then extracted with 2×25 ml ether. The organic layer was collected and washed with 2×10 ml saturated sodium bicarbonate solution and then 3×10 mL water. The organic layer was dried over MgSO4 and concentrated by evaporation. The yield was over 90%. An NMR spectra of 2-methyl-2-[(nitrooxy)methyl]pentyl nitrate and 2-propylpentyl nitrate is shown in FIGS. 1 and 2.

Figure 3A:
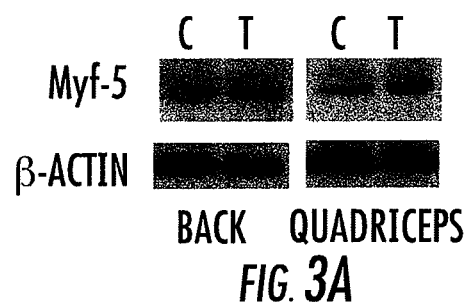
FIG. 3 is a Western blot analysis that shows the expression of Myf-5, myogenin, follistatin, and B-actin proteins in both treated and untreated mice muscle tissue.
Figure 3B:
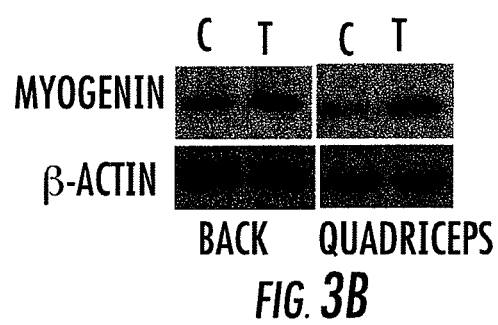
Figure 3C:
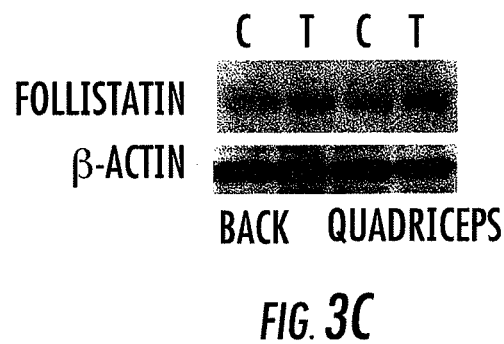

In the first Example, the expression of proteins associated with repair and development of muscle tissue were evaluated. 5-month old mice were orally administered 80 mg/kg body weight of 2-methyl-2-[(nitrooxy)methyl]pentyl nitrate. Muscles of the back and quadriceps were collected at 24 hours following administration. Expression of Myf-5, myogenin, follistatin, and β-actin proteins were evaluated using Western blotting. β-actin was used to evaluate loading control of the active ingredient. Myf-5 and myogenin are members of the well-characterized family of myogenic helix-loop-helix proteins that play an important role in muscle development. When satellite cells are activated and become proliferative, Myf-5 expression is increased. Myogenin expression then marks the subsequent myogenic differentiation processes. Follistatin leads to satellite cell activation, myogenic differentiation and muscle growth by inhibition of myostatin that inhibits satellite-cell activation. The Western Blot results are shown in FIG. 3 where T represents the treated mice and C represents the control mice. As can be seen in FIG. 3, mice treated with the inventive nitrate ester showed an increase in expression of Myf-5, myogenin and follistatin.

The toxicity of the nitrate ester compounds were also evaluated, the results of which are summarized in Table 1 below. In this investigation, normal mice were treated for 24 hours with a single dosage (80 mg/kg body weight) of the inventive nitrate compounds. MDX mice were treated for 90 days in which the mice received a dosage of 80 mg/kg body weight per day. The mice were not treated on the weekends. As can be seen in Table 1, MDX mice treated with the inventive nitrate esters had decreased Serum CK and both the normal mice and MDX mice exhibited no kidney or liver toxicities.

TABLE 1

Mouse serum clinical pathology results after the nitrate ester treatment for normal mice and mdx mice.

| Test | Reference | Placebo/Normal | Treated/Normal | Placebo/mdx | Treated/mdx |
|---|---|---|---|---|---|
| CK (U/L) | 155 | 1161 ± 527 | 1909 ± 258 | 6074 ± 1087 | 4726 ± 763 |
| ALT (U/L) | 44-87 | 30 ± 4 | 52 ± 16 | 112 ± 6 | 136 ± 19 |
| BUN (mg/dL) | 18-31 | 25 ± 4 | 28 ± 4 | 31 ± 3 | 32 ± 2 |
| Creatinine (mg/dL) | 0.48-1.1 | 0.17 ± 0.06 | 0.17 ± 0.06 | 0.15 ± 0.07 | 0.13 ± 0.06 |
| GGT (U/L) | | <3 | <3 | <3 | <3 |
| ALP (U/L) | 43-71 | 43 ± 7 | 40 ± 3 | 64 ± 13 | 65 ± 5 |
| Total Bilirubin (mg/dL) | 0.3-0.8 | 0.27 ± 0.06 | 0.30 ± 0.00 | 0.25 ± 0.07 | 0.27 ± 0.06 |

Figure 4A:
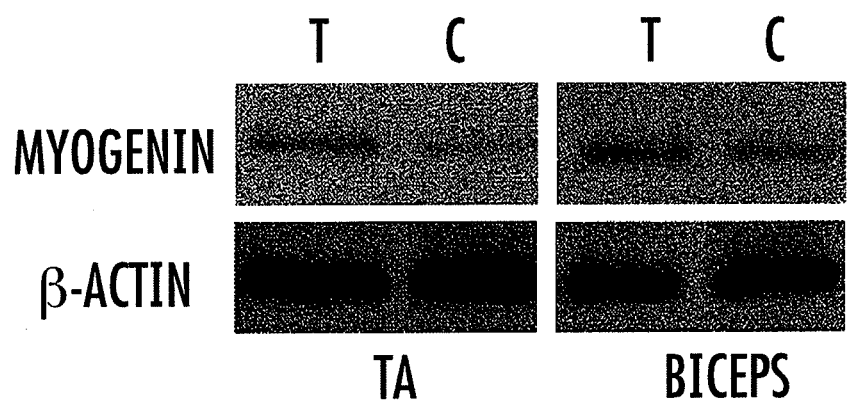
FIG. 4 is a Western blotting analysis of muscle tissues extracted from the biceps and tibialis anterior (TA) of mice for the expression of myogenin and myostatin in both treated and untreated mice muscle tissue.
Figure 4B:
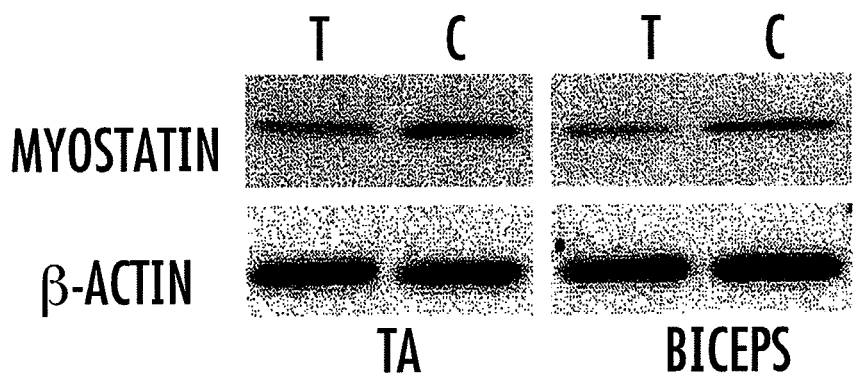

The inventive nitrate esters were also evaluated for their affect on myogenin and myostatin expression. Male mdx mice (one month old) were orally administered the inventive nitrate ester for 90 days (80 mg/kg body weight). The mice were not treated on the weekends. FIG. 4 is a Western blotting analysis of the muscle tissues extracted from the biceps and tibialis anterior (TA) of the mice. The western blot shows that the treatment increased myogenin expression in TA and biceps, and decreased myostatin levels. β-actin was used as the loading control. C and T represent the samples of control and treated animals, respectively.

The inventive compounds were also evaluated for their affects on muscle performance and endurance in dystrophic mice. Male mdx mice (one month old) were gavaged with the nitrate ester compounds daily for 3 months (40 mg/kg body weight). Treadmill and grip strength test were done 2 days after drug treatment. Mice were placed on a four-channel mouse treadmill system (Harvard Apparatus) equipped with a shock plate (setting at 0.6 mA). Mice were first trained for 5 minutes at 5 meters/min and 0° incline. After a 30 min break, running exhaustion test then started. The speed was set at 5 m/min at beginning, and then was increased 1 meters/min every min up to 15 meters/min. The treatment significantly increased the animal's endurance of exercise; Mouse Grip Strength Meter (Columbus Instruments Columbus, Ohio) was used to measure forelimb grip strength. The test was repeated 5 consecutive times within the same session and the highest value from the 5 trials was recorded as the grip strength for that animal. Data are presented as Mean±SEM, n=8, * p<0.05, ** p<0.01. The results are summarized in Table 2 below. As can be seen in Table 2, the treated MDX mice showed significant improvement in endurance and muscle strength.

TABLE 2

Performance Evaluation of MDX mice

| Running time (min) | | Running distance (meter) | | Grip strength (LBF) | |
|---|---|---|---|---|---|
| Treated | Control | Treated | Control | Treated | Control |
| 19.9 ± 2.2* | 13.5 ± 1.0 | 247.7 ± 39.3* | 134.8 ± 15.2 | 0.236 ± 0.014** | 0.174 ± 0.009 |

Figure 5:
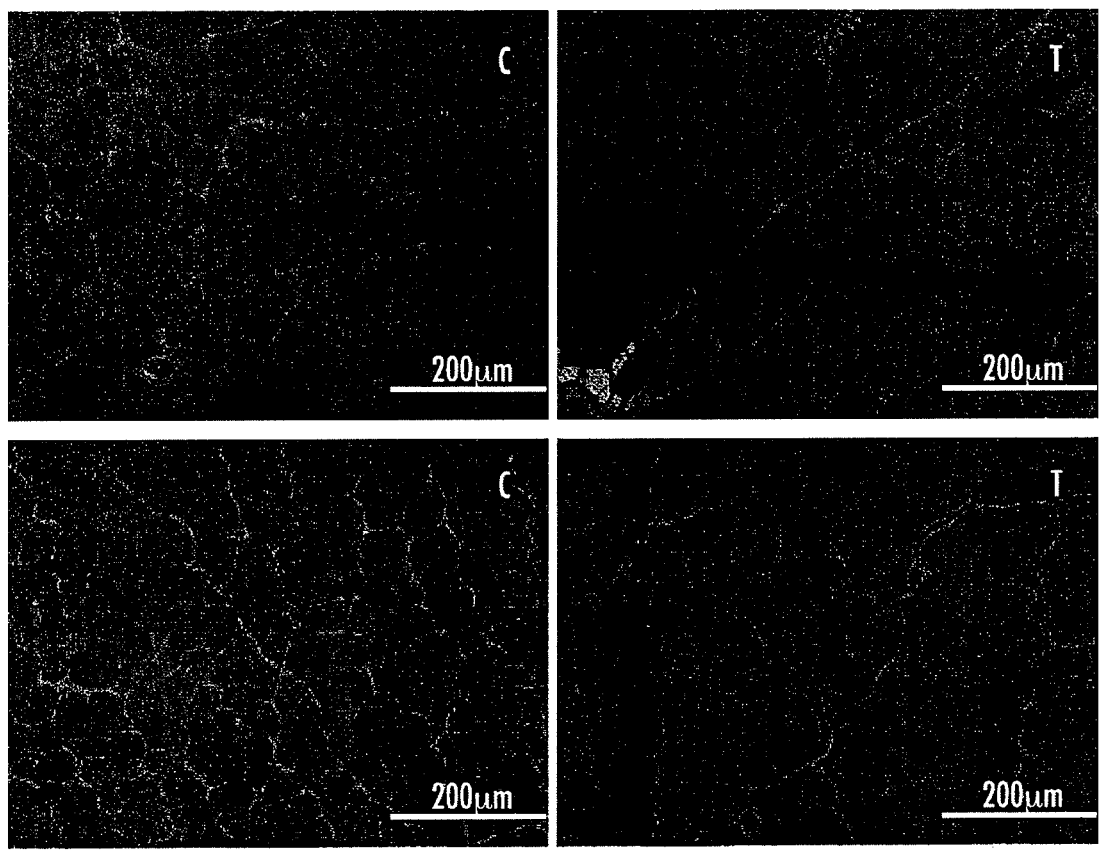
FIG. 5 is a H&E stain of biceps and tibialis anterior muscles of control and treated mice.

The treatment of the inventive compounds was also shown to significantly reduces tissue inflammation and degradation in dystrophic mice. Male mdx mice (one month old) were gavaged with the nitrate ester daily for 3 months (40 mg/kg body weight). As shown in FIG. 5, H&E staining of biceps (up panel) and tibialis anterior (low panel) muscles show significant reduction of tissue inflammation and degradation. C and T represent the samples of control and treated mice respectively.

The inventive compounds were also evaluated for their affects on neuromuscular properties in dystrophic mice. Central nuclearation is determined by the ratio of the number of the fibers with centered nuclei over the number of total fibers in a field. 8 randomly selected fields were counted; Cross section area (CSA) is determined by measuring shortest muscle fiber diameter. 20 fibers each from four corner and centre areas in a field were measured, totally 800 fibers from 8 randomly selected fields were determined by using the NIH software Image J; Vascular density of TA is presented as capillary-to-muscle fiber ratio by dividing the number of capillaries with the number of muscle fibers from 8 randomly selected fields. Vascular density of heart is presented as the number of capillaries per field by counting capillaries from 8 randomly selected fields. The results are shown in Table 3. Data are presented as Mean±SE, * p≤0.05, *** p≤0.001.

TABLE 3

Neuromuscular assessment of 3 months treatment in mdx mice:

| Determination | Treatment | Control |
|---|---|---|
| Central nuclearation (TA) | 70 ± 3%* | 79 ± 2% |
| Diameter (mm, TA) | 20.7 ± 0.2*** | 19.7 ± 0.2 |
| Vascular density (TA) | 0.69 ± 0.03* | 0.53 ± 0.06 |
| Vascular density (Heart) | 265 ± 38* | 235 ± 40 |

6 Data are presented as Mean ± SE, *p ≤ 0.05, ***p ≤ 0.001.

The inventive compounds were also evaluated to determine effects in the muscle performance in old normal mice (11 months). The inventive nitrate formulation was administered orally to 11 months old normal mice for 2 weeks (4 males and 4 females in each group). The muscular functions were assessed by grip strength meter and treadmill. The results are summarized in Table 4 below. As can be seen from the results summarized in Table 4, the nitrate ester compounds enhance exercise performance in the mice.

TABLE 4

Evaluation of Exercise Performance in normal mice.

| Determination | Treatment | Control |
| --- | --- | --- |
| Treadmill (min) | 128 ± 31* | 82 ± 16 |
| Treadmill (meters) | 2019 ± 557* | 1269 ± 255 |
| Grip strength (LBF) | 0.327 ± 0.019* | 0.0.287 ± 0.013 |

The treatment of inventive compounds was also shown to reduce serum lactate concentration in normal and dystrophic mice. The compound formulation was administered orally to 7 months old normal mice and 5 months dystrophic mice for 2 weeks (40 mg/kg body weight). Serum lactate contents were assayed. The results are summarized in Table 5 below.

TABLE 5

Evaluation of Nitrate Ester affects on Lactate Concentration

| Lactate (mM) | Treatment | Control |
| --- | --- | --- |
| C57 mice | 5.25 ± 0.20* | 6.10 ± 0.40 |
| Dystrophic mice | 6.70 ± 0.22* | 7.45 ± 0.13 |

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for treating a muscular-related genetic disease comprising administering to a subject an effective amount of one or more of 2-methyl-2-[(nitrooxy)methyl]pentyl nitrate or 2-propylpentyl nitrate,
    wherein the muscular-related genetic disease includes a genetic mutation of pathways involving genes for muscular regulatory proteins.
2. The method of claim 1, wherein further comprising the step of administering a muscle relaxant to the subject.
3. The method of claim 2, wherein the muscle relaxant is methocarbamol.
4. The method of claim 1, wherein the compound is administered at a dosage from about 2 mg to 80 mg/kg body weight.
5. The method of claim 1, wherein the compound wherein the compound is administered orally.
6. A method for treating a muscle related genetic disease comprising administering to a patient a therapeutically effective amount of a compound selected from the group consisting of:
    2-methyl-2-[(nitrooxy)methyl]pentyl nitrate, 2-propylpentyl nitrate, and combinations thereof, and wherein the muscular-related genetic disease is disease is muscular dystrophy.
7. A pharmaceutical composition for the treatment of dystrophic muscle related injuries or disease, the composition comprising 2-propylpentyl nitrate.
8. The method of claim 1, wherein for muscular regulatory proteins include MyoD, myf5, myogenin, pax7, and follistan.

* * * * *